(12) United States Patent
Shao et al.

(10) Patent No.: US 6,958,231 B2
(45) Date of Patent: Oct. 25, 2005

(54) **VARIANTS OF *ERWINIA*-TYPE CREATINASE**

(75) Inventors: Zhixin Shao, Penzberg (DE); Rainer Schmuck, Benediktbeuern (DE); Peter Kratzsch, Antdorf (DE); Janet Kenklies, Penzberg (DE); Harald Weisser, Bernried (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 102 days.

(21) Appl. No.: 10/251,078

(22) Filed: Sep. 20, 2002

(65) Prior Publication Data

US 2003/0119084 A1 Jun. 26, 2003

(30) Foreign Application Priority Data

Sep. 20, 2001 (EP) .............................. 01121780

(51) Int. Cl.⁷ ............................. C12N 9/78; C12N 9/02; C07H 21/04
(52) U.S. Cl. ........................ 435/227; 435/189; 536/23.2
(58) Field of Search ................................ 435/227, 189; 536/23.2

(56) References Cited

U.S. PATENT DOCUMENTS

| 4,420,562 A | | 12/1983 | Ikuta et al. .................. 435/227 |
| 5,451,520 A | | 9/1995 | Furukawa et al. ........... 435/227 |
| 6,080,553 A | * | 6/2000 | Sogabe et al. ................. 435/18 |

FOREIGN PATENT DOCUMENTS

| DE | 26 59 878 A1 | 11/1977 |
| EP | 0 291 055 A2 | 5/1988 |
| EP | 0 790 303 A1 | 8/1997 |
| NL | 30 24 915 A1 | 1/1981 |

OTHER PUBLICATIONS

Beyer, C., et al, *Measurement of Creatine in Urine by Creatinase, Sarcosine Oxidase, and Peroxidase Reevaluated*, Clinical Chemistry, vol. 39, No. 8, pp. 1743–1744 (1993).

Cadwell, R. Craig, et al, *Mutagenic PCR*, PCR Methods and Applications, vol. 3, pp. S136–S140 (1994).

Feng, Da–Fei, et al, *Progressive Sequence Alignment as a Prerequisite to Correct Phylogenetic Trees*, J. Mol. Evol, vol. 25, pp. 351–360 (1987).

Fujita, T., et al, *Enzymatic Rate Assay of Creatinine in Serum and Urine*, Clinical Chemistry, vol. 39, No. 10, pp. 2130–2136 (1993).

Guder, W., et al, *Multicentre Evaluation of an Enzymatic Method for Creatinine Determination Using a Sensitive Colour Reagent*, J. Clin. Chem. Biochem, vol. 24, pp. 889–902 (1986).

Hong, Ming Chuan, et al, *Expression and Export of Pseudomonas putida NTU–8 Creatinase by Escherichia coli Using the Chitinase Signal Sequence of Aeromonas hydrophilia*, Biochemical Genetics, vol. 36, Nos, 11/12, pp. 407–415 (1998).

Kaplan, A., et al, *Creatinine Hydrolase and Creatine Amidnohydrolase: II. Partial Purification and Properties*, Molecular & Cellular Biocehmistry, vol. 3, No. 1, pp. 17–25 (1974).

Kaplan, A., et al, *Creatine Hydrolase and Creatine Amidinhoydrolaes: I. Presence in Cell–Free Extracts of Arthrobacter Ureafacines*, Molecular & Cellular Biochemistry, vol. 3, No. 1, pp. 9–15 (1974).

Khan, G.F., et al, *A Highly Sensitive Amperometric Creatinine Sensor*, Analytica Chmicia Acta 351, pp. 151–158 (1997).

Kim, Eun Ju, et al, *Disposable Creatinine Sensor based on thick–film hydrogen peroxide electrode system*, Analytica Chimica Acta 394, pp. 225–231 (1999).

Kopetzki, Erhard, et al, *Enzymes in Diagnostics: Achievements and Possibilities of Recombinant DNA Technology*, Clinical Chemistry, vol. 40, No. 5, pp. 688–704 (1994).

Koyama, Yasuji, et al, *Cloning and Expression of the Creatinase Gene from Flavobacterium sp. U–188 in Escherichia coli,*, Agric. Biol. Chem, vol. 54 (6), pp. 1453–1457 (1990).

Matsuda, Yasuchka, et al, *Purification and Characterization of Creatine Amidinohydrolase of Alcaligenes Origin*, Chem. Pharm., Bult., 34:vol. 5, pp. 2155–2160 (1986).

Y. Nishiya, et al, *Gene cluster for creatinine degradation in Arthrobacter sp. TE1826*, Mol. Gen. Genet, 257, pp. 581–586 (1998).

Patent Abstracts of Japan; vol. 1998, No. 11, Sep. 30, 1998 & JP 10174585 A (Toyobo Co. Ltd.); Jun. 30, 1998.

Schumacher G. et al., "Engineering Enzymes For Clinical Diagnosis"; Ann Biol Clin; vol. 50 (1993) pp. 815–819.

European Search Report ; Application No. EP 02020793; Dec. 6, 2003.

Schumann, Judith, et al, *Intrinsic Stability and Extrinsic Stabilization of Creatinase from Psudomonas putida*, Biol Chem, vol. 374, pp. 427–434 (1993).

Schumann, Judith, et al, *Stabilization of creatinase from Pseudomonas putida by random mutagenesis*, Protein Science 2, pp. 1612–1620 (1993).

(Continued)

*Primary Examiner*—Elizabeth Slobodyansky
(74) *Attorney, Agent, or Firm*—McDonnell Boehnen Hulbert & Berghoff LLP

(57) ABSTRACT

The present invention relates to mutated genes encoding variants of an *Erwinia*-type creatinase (EC 3.5.3.3, alternative name: creatine amidinohydrolase), to the creatinase variants encoded by these genes, and to different applications of these variants of creatinase, particularly to their use for determining the creatinine and/or creatine concentration in a sample.

9 Claims, 2 Drawing Sheets

OTHER PUBLICATIONS

Siedel, Joachim, et al, *Sensitive Color Reagent for the Enzymic Determination of Creatinine*, Abstract 147, Clinical Chemistry, vol. 30, No. 6, pp. 968–969 (1984).

Spencer, Kevin, *Analytical reviews in clinical biochemistry: the estimation of creatinine*, Ann Clin Biochem; 23: pp. 1–25 (1986).

Suzuki, Koji, et al, *Molecular Cloning and High Expression of the Bacillus Creatinase Gene in Escherichia coli*, Journal of Fermentation and Bioengineering, vol. 76, No. 2, pp. 77–81 (1993).

* cited by examiner

Figure 1: Expression vector comprising a creatinase gene
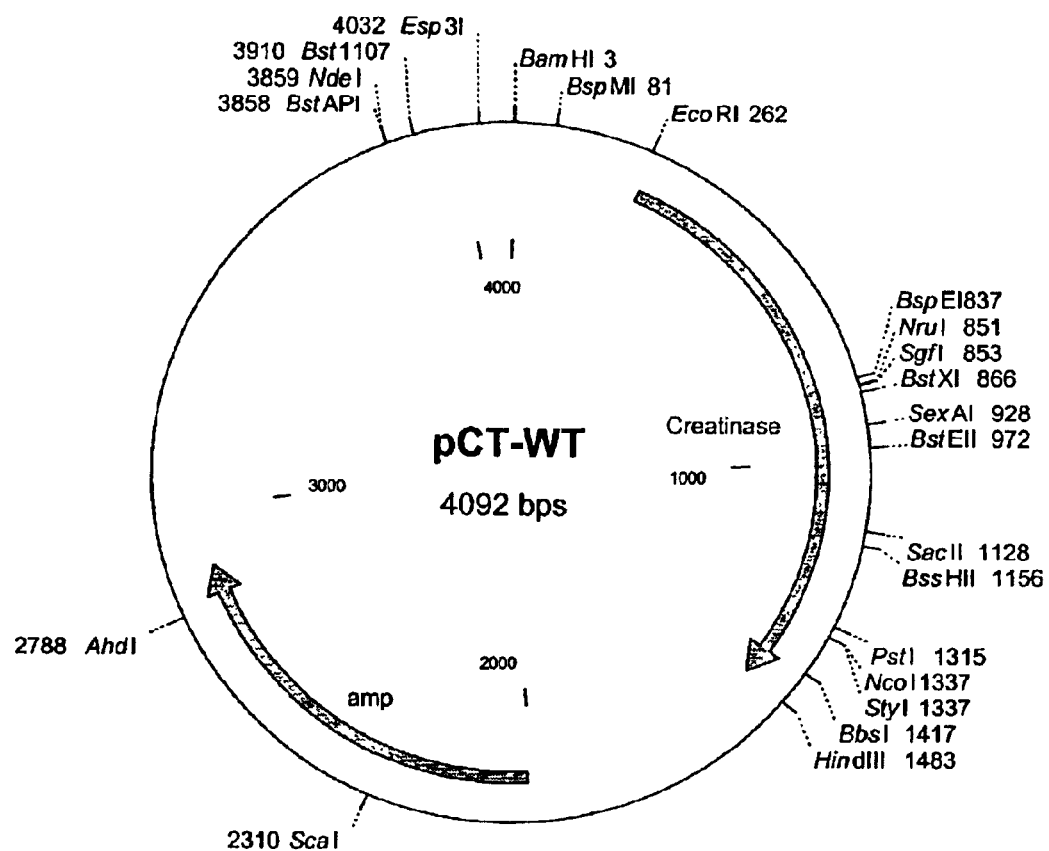

Figure 2    Short-term thermal stress
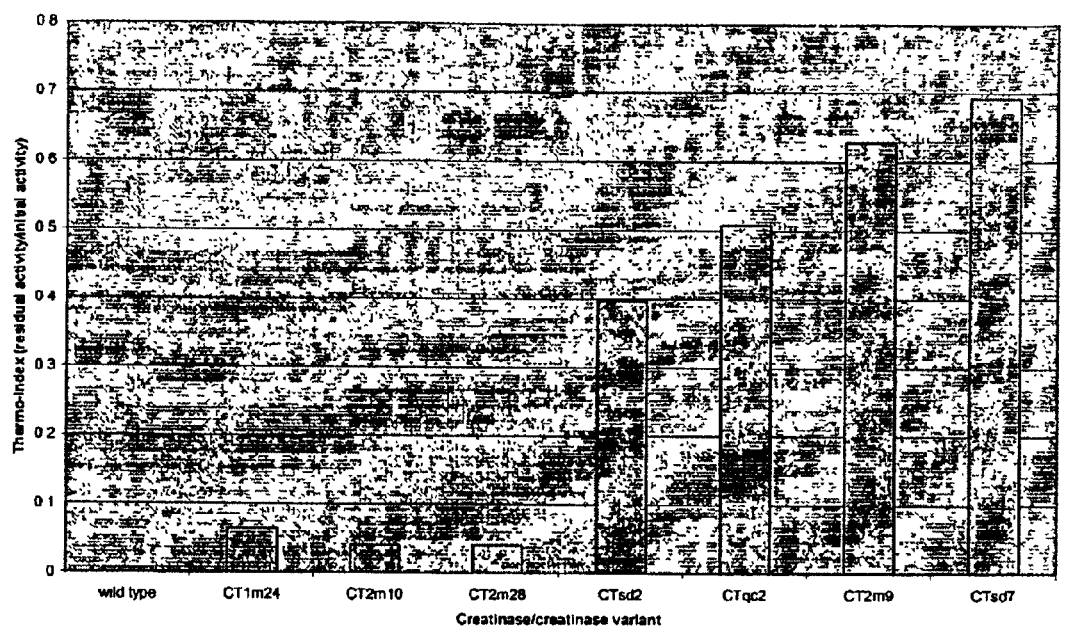

VARIANTS OF ERWINIA-TYPE CREATINASE

FIELD OF THE INVENTION

The present invention relates to mutated genes encoding variants of an be Erwinia-type creatinase (EC 3.5.3.3, alternative name: creatine amidinohydrolase), to the creatinase variants encoded by these genes, and to different applications of these variants of creatinase, particularly to their use for determining the creatinine and/or creatine concentration in a sample.

BACKGROUND OF THE INVENTION

Creatine and creatinine are usually found in blood and urine, and can be used as very important parameters for diagnosing uremia, chronic nephritis, acute nephritis, gigantism, tonic muscular dystrophy and some other related diseases. For such routine diagnostic purposes, creatinine and creatine concentrations in blood and urine need to be determined quickly and accurately (Schumacher, G., et al., Ann Biol Clin 51 (1993) 815–9, Fujita, T., et al., Clin Chem 39 (1993) 2130–6, Spencer, K., Ann Clin Biochem 23 (1986) 1–25).

Generally, creatinase catalyses the hydrolysis of creatine (e.g. as generated from creatinine through creatinase) to urea and sarcosine. In the presence of sarcosine oxidase, sarcosine is oxidized and hydrogen peroxide is generated. The hydrogen peroxide formed is determined by a standard procedure for measurement of hydrogen peroxide, e.g. by a colorimetric procedure catalyzed by horse-radish peroxidase. Through these coupled reactions, creatinine and/or creatine in a sample can be quickly and quantitatively determined (Kopetzki, E., et al., Clin Chem 40 (1994) 688–704, Beyer, C., et al., Clin Chem 39 (1993) 174–34).

Enzymes with creatinase activity have been found in different microorganisms, including Arthrobacter (Kaplan, A. Szabo, L. L., Mol Cell Biochem 3 (1974) 17–25, Kaplan, A. Naugler, D., Mol Cell Biochem 3 (1974) 9–15, Nishiya, Y., et al., Mol Gen Genet 257 (1998) 581–6), Bacillus (Suzuki, K., et al., Journal of Fermentation & Bioengineering 76 (1993) 77–81), Alcaligenes (Matsuda, Y., et al., Chem. Pharm. Bull. 34 (1986) 2155–2160), Pseudomonas (Hong, M. C., et al., Biochem Genet 36 (1998) 407–15) and Flavobacterium (Koyama, Y., et al., Agric Biol Chem 54 (1990) 1453–7).

Several creatinase enzymes obtained from different microorganisms have been industrially produced and used as reagents for clinical tests. However, even with state-of-the-art creatinase enzymes and/or with state-of-the-art creatine assays, the creatinase enzyme is generally the major limiting factor for or in such assays.

Important criteria for broad industrial, especially diagnostic applicability, comprise solubility, conductivity (in case of electronic signal generation and measurement), stability, and enzymatic activity with creatine as substrate. Obviously, stability (e.g., short-term heat stability or long-term storage stability) and enzymatic activity are especially relevant or critical in routine applications. Schumann et al. (Schumann, J., et al., Biol Chem Hoppe Seyler 374 (1993) 427–344) showed that "extrinsic factors", such as DTE, bovine serum albumin (BSA) and glycerol, can improve the stability of P. putida creatinase. But these extrinsic factors are generally not compatible with the conditions for a coupled creatinine and/or creatine assay system using creatinase, creatinase, sarcosine oxidase and peroxidase.

All the native or wild-type creatinase enzymes known from the art exhibit certain limitations with regard to thermostability and their Km value for creatine. For example, the enzyme derived form the Bacillus is unstable at any temperature of more than 40° C. (see patent U.S. Pat. No. 4,420,562). The creatinase from Pseudomonas putida has both, rather low storage stability (Schumann, J., et al., supra) and a rather high Km value (see patent EP 0 291 055), and, consequently, the enzyme is not suitable for creatine determination in a liquid formulation as required in the coupled creatine assay mentioned above using also sarcosine oxidase and peroxidase as auxiliary reagents.

Creatinases isolated from Corynebacterium (see patent DE 2 659 878), Micrococcus, or Bacillus (see patent DE 3 024 915) have been found unstable at elevated temperatures and, therefore are not suitable for the formulation of long-term stable liquid assay reagents, either. A creatinase from Alcalingenes has been reported to have a Km value of 13 mM and to be stable at a temperature of 45° C. for 30 minutes (see patent U.S. Pat. No. 5,451,520).

There are few literature reports about engineered creatinases (Schumann, J., et al., Protein Sci 2 (1993) 1612–20) used random and site-directed mutagenesis to introduce point mutations into P. putida creatinase in order to generate mutants with an altered stability profile. Three point mutants with A109V, V355M, or V182I, one double mutant with A109V and V355M, and one triple mutant with all three substitutions in P. putida creatinase were generated and compared to the wild-type enzyme regarding their physical and enzymological properties. Physicochemical measurements showed that the mutations exhibit only a small increase in overall stability. Even the best mutant, however, is not stable at elevated temperature, e.g. temperatures of 45° C. and above. The catalytic properties are in the range of the wild-type enzyme or are inferior.

EP 0 790 303 describes a process of generating Alcaligenes faecalis creatinase variants with lower Km values as compared to the wild-type enzyme using the in vivo mutagenesis approach in E. coli strain XL1-Red (Stratagene, CaL Nr. 200 129). The Km values of the creatinase variants were found to range from 4.5 mM to 9.0 mM.

It can be summarized that the attempts known from the art, e.g., as discussed above, either aiming at the isolation and purification of creatinase from various microorganisms or at the genetic improvement of such enzymes, to date still have led to enzymes lacking important industrial properties.

A great demand and clinical need therefore exists for mutant forms of creatinase with improved properties, especially regarding improved stability and/or lower Km-value to its substrate creatine.

It was the task of the present invention to provide new mutants or variants of creatinase with significantly lower Km-value or significantly improved stability, or both.

Surprisingly it has been found that it is possible to provide such creatinase enzymes by mutating one or several amino acids of an Erwinia-type creatinase at precisely defined positions. Such relevant positions are defined and given as amino acid positions corresponding to amino acid positions of the wild-type creatinase isolated from Erwinia sp. DSM 97-934.

SUMMARY OF THE INVENTION

The present invention relates to a variant of an Erwinia-type creatinase modified relative to a wild-type creatinase having creatinase activity, characterized in that said variant comprises at least one amino acid substitutions at a position corresponding to a position selected from the group of positions consisting of N130, M203, I278, I304, and F395 of the amino acid sequence shown in SEQ ID NO:2.

The variant creatinases according to the present invention exhibit improved properties as compared to the respective wild-type enzymes. Improved variants are described, exhibiting either individually or as a combination of such improved properties, like lower conductivity, improved stability, or lower Km-value for creatine.

The present invention also relates to a reagent for determination of creatine comprising a creatinase as described in the present invention. It especially relates to a reagent, which comprises a creatinase variant and also comprises a sarcosine oxidase as well as reagents for the detection of hydrogen peroxide.

Due to the significantly improved properties as compared to wild-type or mutated enzymes known in the art, the variant creatinase according to the present invention is used with great advantage in a method for detection of creatine.

DESCRIPTION OF THE FIGURES

FIG. 1 This figure shows an expression vector comprising the gene of SEQ ID NO: 1 coding for the full length creatinase of SEQ ID NO:2. The expression vector is known in the art as pCT.

FIG. 2 This figure shows the short term thermal stress stability of the wild-type creatinase isolated from *Erwinia* sp. (DSM 97-934) and of variants according to the present invention. The stability is assessed by calculating a "Thermo-Index". This index is obtained by calculating the residual enzymatic activity after short term heat stress in relation to the activity without heat stress.

DETAILED DESCRIPTION OF THE INVENTION

In a first embodiment the present invention relates to a variant of an *Erwinia*-type creatinase modified relative to a wild-type creatinase having creatinase activity, characterized in that said variant comprises at least one amino acid substitutions at a position corresponding to a position selected from the group of positions consisting of N130, M203, I278, I304, and F395 of the amino acid sequence shown in SEQ ID NO:2.

The present invention relates to improved variants of an *Erwinia*-type creatinase. An "*Erwinia*-type creatinase" is defined by at least 85 % sequence identity on the amino acid level as compared to SEQ ID NO:2.

The terminology used, for example N130, indicates that the amino acid asparagine (N) of position 130 in SEQ ID NO:2 is referred to. If the amino acid position is followed by one or more amino acids (as described by single letter code) for example, N130 D, E this indicates that the amino acid arginine found in wild-type position 130 has been substituted either by aspartic acid (D) or glutamic acid (E).

Creatinase (creatine amidinohydrolase, EC3.5.3.3) catalyzes the hydrolytic cleavage of creatine to sarcosine and urea. An enzyme with this catalytic activity is defined in the art as having creatinase activity.

The use of creatinase enzymes is highly important in medical diagnostics because it is used to assess creatinine as well as creatine concentrations. Especially important is the assessment of creatinine clearance, which is used to monitor kidney function. The enzyme creatinase catalyzes the second step in such a coupled creatinine-creatine assay (Siedel, J., et al., Clinical Chemistry 30 (1984) 968–969).

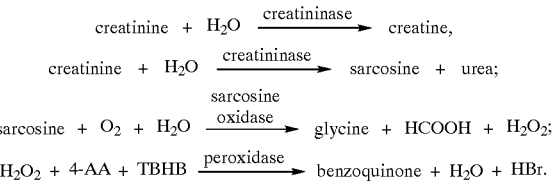

As is obvious from the above reaction schemes creatinase may be used in the detection of creatine alone or in the combined detection of creatinine and creatine. The hydrogen peroxide ($H_2O_2$) generated upon the action of sarcosidase is measured.

Preferably a dye system is used comprising a coupler reagent (e.g. as above 4-AA=4-Amino-2,3-dimethyl-1-phenyl-3-pyrozoline-5-one) and a color generating substance (e.g. as above TBMB=2,4,6-tribromo-3-hydroxybenzoic acid) which upon action of peroxidase produces a color signal (benzoquinone) proportional to the peroxide concentration and thus proportional to the concentration of creatinine and creatine in the sample analyzed.

The present invention is based on the surprising finding that variants of wild-type creatinase can be provided, which represent significant improvements as compared to the corresponding wild-type enzyme. The improvements according to the present invention are described based on the amino acid composition and numbering of the creatinase enzyme as isolated from *Erwinia* species (DSM 97-934). The wild-type enzyme from this *Erwinia* species has been cloned, sequenced (SEQ ID NO:1) and the protein sequence found to correspond to SEQ ID NO:2.

It has been found that amino acid substitutions in amino acid positions F59, N113, N203, I278, I304, and F395 of SEQ ID NO:2 are particularly relevant to produce enzyme variants with improved properties. Comparative sequence analysis using amino acid sequence motifs of 7 amino acids in length and comprising the above identified critical amino acid position in their center, revealed that corresponding positions can be identified in creatinases isolated from various other organisms. Obviously, the mutations described in the present invention can also be used to modify corresponding sequence positions of other known and yet unidentified creatinases. The term "corresponding to a position" is used to indicate that creatinase enzymes and variants thereof may also be found or generated comprising additional amino acids or lacking amino acids, which upon sequence alignment to SEQ ID NO:2 results in a different absolute number for the corresponding sequence position or motif.

The multiple alignment and comparison of *Erwinia* creatinase with other related creatinases has been performed with the PileUp program of GCG Package Version 10.2 (Genetics Computer Group, Inc.). PileUp creates a multiple sequence alignment using a simplification of the progressive alignment method of Feng, D. F. Doolittle, R. F., J Mol Evol 25 (1987) 351–60, and the scoring matrixes for identical, similar, or different amino acid residues are defined accordingly. This process begins with the pairwise alignment of the two most similar (creatinase) sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments that include increasingly dissimilar sequences and clusters, until all sequences have been included in the final pairwise alignment.

A variant of an *Erwinia*-type creatinase in the sense of the present invention is a modified creatinase enzyme, which relative to its wild-type sequence comprises at least one amino acid substitution at a position, which corresponds to a position selected from the group of positions consisting for N130, N203, I278, I304, and F395 of SEQ ID NO:2.

In case the wild-type enzyme does not comprise a tryptophanc(W) residue in position 59, the preferred creatinase variant may additionally be modified to comprise W in position 59. A preferred *Erwinia*-type creatinase variant according to the present invention therefore contains the amino acid substitution F59W and at least one further amino acid substitution selected from the group of positions corresponding to N130, N203, I278, I304, and F395 of SEQ ID NO:2.

The positions corresponding to the above mentioned positions of SEQ ID NO:2 from related creatinase enzymes can easily be found by sequence alignment using the following sequence motifs: 56–62 (SEQ ID NO:3), 127–133 (SEQ ID NO:4), 200–206 (SEQ ID NO:5), 275–281 (SEQ ID NO:6), 301–307 (SEQ ID NO:7), and 392–398 (SEQ ID NO:8). These positions correspond if six out of seven amino acids are identical.

A preferred variant of an *Erwinia*-type creatinase according to the present invention comprises a mutation in an amino acid position corresponding to position N130 of SEQ ID NO:2. Preferably the amino acid residues introduced by substitution are polar residues or charged residues. Preferred are creatinase variants comprising the substitution N130E or N130D, the variant comprising N130D being most preferred.

A preferred variant of an *Erwinia*-type creatinase according to the present invention comprises a mutation in an amino acid position corresponding to position M203 of SEQ ID NO:2. Preferably the amino acid residues introduced by substitution are aliphatic residues. Preferred are creatinase variants comprising the substitution M203V, M203I or M203L, the variant comprising M203V being most preferred.

A preferred variant of an *Erwinia*-type creatinase according to the present invention comprises a mutation in an amino acid position corresponding to position I278 of SEQ ID NO:2. Preferably the amino acid residues introduced by substitution are small polar residues or small hydrophobic residues. Preferred are creatinase variants comprising the substitution I278T, I278S, I278V or I278G, the variant comprising I278T being most preferred.

A preferred variant of an *Erwinia*-type creatinase according to the present invention comprises a mutation in an amino acid position corresponding to position I304 of SEQ ID NO:2. Preferably the amino acid residues introduced by substitution are aliphatic residues. Preferred are creatinase variants comprising the substitution I304L or I304V, the variant comprising I304L being most preferred.

A preferred variant of an *Erwinia*-type creatinase according to the present invention comprises a mutation in an amino acid position corresponding to position F395 of SEQ ID NO:2. Preferably the amino acid residues introduced by substitution are aliphatic residues. Preferred are creatinase variants comprising the substitution F395L, F395I, or F395V, the variant comprising F395L being most preferred.

In a further preferred embodiment the variant of an *Erwinia*-type creatinase according to the present invention comprises at least two substitutions which corresponds to a position selected from the group of positions consisting of N130, N203, I278, I304, and F395 of SEQ ID NO:2.

In a preferred embodiment a variant of an *Erwinia*-type creatinase according to the present invention comprises a substitution of at least one of the amino acids corresponding to positions N130 or I278.

Substitutions of amino acids at positions corresponding to 130 or 278 of SEQ ID NO:2 have been found extremely important to increase the stability of an *Erwinia*-type creatinase variant.

A further preferred *Erwinia*-type creatinase variant comprises at least one substitution at an amino acid position corresponding to position 130 by D or E (aspartic or glutamic acid) or position 278 by threonine (T). A variant comprising substitutions at both the above discussed amino acid positions represents a further preferred embodiment.

The term "stability" in general is used to describe many different properties like pH-tolerance, salt tolerance or thermal inactivation. According to the present invention stability relates to heat or to storage stability. Heat or storage stability is easily analyzed using appropriate model systems.

In a further preferred embodiment the variant of an *Erwinia*-type creatinase according to the present invention is characterized in that said variant exhibits improved long-term storage stability.

Storage stability relates to the long term stability of reagents, e.g. to stability under storage for several moths or a few years. The long-term storage stability is assessed by treating a solution containing creatinase for 21 days at 35° C. Stability in this model system is known to correspond to a storage stability of at least 18 months using storage temperatures between 4 and 8° C. A creatinase variant is considered stable if after storage according to this model at least 90 % of the original enzymatic activity are still found. With the improved variants according to the present invention at least 90 % of the original enzymatic activity are left and can be measured by routine procedures.

Heat stability is assessed in a short-term stress model, for example by incubation of the enzyme at 56° C. for 20 minutes. Such a short-term stress model is very important to decide, whether reagents may be shipped at ambient temperature or whether cooling is required. A creatinase or a variant thereof is defined as meeting these arbitrary stability criteria (i.e., the short-term thermal stress stability criteria) if after 20 minutes at 56° C. at least 30 % of the original creatinase activity is left. A preferred variant of creatinase according to the present invention exhibits improved stability at 56° C. I. e., after incubation at 56° C. for 20 minutes at least 30 % of the original activity are left.

Variants of an *Erwinia*-type creatinase have been found, which exhibit improvements both with respect to both short-term thermal stress, i.e. heat stability as well as to long-term storage stability. Such variants exhibiting improved stability, both under heat stress and under long-term storage conditions represent a further preferred embodiment of the present invention.

In a further preferred embodiment according to the present invention the variant of an *Erwinia*-type creatinase is characterized in that it comprises an amino acid substitution in at least one of the positions corresponding to I304 or F395 of SEQ ID NO:2.

As is known from the state of the art (see above) the catalytic property for cleavage of creatine of the various creatinases so far at hand is considered critical. One of these catalytic properties is most easily expressed in terms of Km-values.

The Km-value of an enzyme reflects both the binding affinity between enzyme and substrate and the rate at which the enzyme-bound substrate is converted to the corresponding reaction product. The higher the Km-value, the lower is the catalytic efficiency of an enzyme. It surprisingly has been found that amino acid positions corresponding to position 304 and 395 of SEQ ID NO:2 are very important in order to generate variants of creatinase with improved, i.e., lower Km-values. In a preferred embodiment the variant of an *Erwinia*-type creatinase comprises at least one amino acid substitution at an amino acid position corresponding to 304 by the amino acid L, or V, or position 395 by the amino acid L, I, or V.

An *Erwinia*-type creatinase variant with lower Km-value for creatine comprising substitutions at both the amino acid positions corresponding to 304 and 395 of SEQ ID NO:2 represents a further preferred embodiment.

A variant creatinase which is characterized by having a lower Km-value in the enzymatic cleavage of creatinine represents a further preferred embodiment. The Km-value of a creatinase variant is either assessed in comparison to the corresponding wild-type enzyme or given in absolute terms as Km-value. The Km-value is determined by routine procedures, for example using the reagents as described in Example 7.

An *Erwinia*-type creatinase according to the present invention preferably exhibits a Km-value which compared to the corresponding wild-type enzyme is 80% or less, more preferred 65% or less and most preferred 50% or less of the Km-value as determined for the corresponding wild-type enzyme.

An *Erwinia*-type creatinase according to the present invention in absolute terms preferably exhibits a Km-value of less than 10 mM, more preferred of less than 4 mM and most preferred of less than 2.5 mM.

It has been found that some of the improvements in terms of stability go to the expense of the Km-value (see Table 4). Interestingly and surprisingly, it has been also been found that by including the appropriate "catalytic property mutations" as discussed above, into a variant which exhibits improved stability properties, creatinase variants can be designed with advantageous properties in both respects. In a preferred embodiment the *Erwinia*-type creatinase variant is characterized in that said variant comprises at least one amino acid substitution at a position corresponding to a position in the amino acid sequence shown in SEQ ID NO: 1, selected from the positions N130 and I278 as well as at least one substitution at a position corresponding to a position of SEQ ID NO:2 selected from the positions I304 and F395

An *Erwinia*-type creatinase variant comprising substitutions in the position corresponding to N130, M203 and I278 of SEQ ID NO:2 represents a further preferred embodiment according to the present invention. Preferably this variant comprises N130D, M203V and I278T.

In a preferred embodiment the variant creatinase according to the present invention exhibits both improved stability and a lower Km-value in the enzymatic cleavage of creatine as compared to the wild-type creatinase obtained from *Erwinia* spec. (DSM97-934).

A creatinase variant according to the present invention can e.g., be produced by starting from a creatinase gene as isolated from *Erwinia* spec. DSM 97-934 as well as by starting from a homologous sequence. In the context of this application the term "homologous" is meant to comprise wild-type creatinases as isolated from other microorganisms, provided that the sequence homology as compared to SEQ ID NO:2 is at least 85 %. With other words, after appropriate alignment using the PileUp program, at least 85 % of the amino acids of that creatinase are identical to the amino acids described in SEQ ID NO:2.

It will be understood that variations of DNA and amino acid sequences naturally exits, or may be intentionally introduced using methods known in the art. These variations may result in up to 15 % amino acid differences in the overall sequence, due to deletions, substitutions, insertions, inversions or additions of one or more amino acid residues in said sequence as compared to SEQ ID NO:2. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substitution such as methionine, N-formylmethionine used as leader sequences. Such variations may be made without necessarily departing from the scope and the spirit of the present invention.

Procedures for isolating a creatinase gene from a microorganism as well as operations and methods used for the purification, characterization, and cloning of relevant DNA are well known in the art (e.g., EP 0 790 303 and Ausubel, F., et al. in "Current Protocols in Molecular Biology" (1994) Wiley Verlag).

Based on the identification of critically important amino acid positions as described in the present invention the skilled artisan now can easily produce further appropriate variants of creatinase.

The present invention further includes an expression vector comprising a nucleic acid sequence of the invention operably linked to a promoter sequence capable of directing its expression in a host cell. Preferred vectors are plasmids such as pKK177-3HB. A vector containing the wild-type *Erwinia* creatinase gene is shown in FIG. 1 (pCT-WT).

Expression vectors useful in the present invention typically contain an origin of replication, a promoter located in front (i.e., upstream of ) the DNA sequence and followed by the DNA sequence coding for all or part of creatinase variants. The DNA sequence coding for all or part of the creatinase variants is followed by transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and the sequences which provide sites for cleavage by restriction endonucleases. The characteristics of the actual expression vector used must be compatible with the host cell which is to be employed. For example, when cloning in an *E. coli* cell system, the expression vector should contain promoters isolated from the genome of *E. coli* cells (e.g., tac, lac, or trp). Suitable origins of replication in *E. coli* various hosts include, for example, a ColEI plasmid replication origin. Suitable promoter include, for example, the tac, lac, and trp. It is also preferred that the expression vector include a sequence coding for a selectable marker. The selectable marker is preferably antibiotic resistance. As selectable markers, ampicillin resistance, or kanamycin resistance may be conveniently employed. All of these materials are known in the art and are commercially available.

Suitable expression vectors containing the desired coding and control sequences may be constructed using standard recombinant DNA techniques known in the art, many of which are described in Sambrook et al. (Sambrook, J., et al. —in "Molecular Cloning: A Laboratory Manual" (1989) —, Cold Spring Harbour, N.Y., Cold Spring Harbour Laboratory Press).

The present invention additionally concerns host cells containing and expression vector which comprises a DNA sequence coding for all or part of the mutant creatinase. The host cells preferably contain an expression vector which comprises all or part of one of the DNA sequences having one or more mutations. Further preferred are the host cells containing an expression vector comprising one or more regulatory DNA sequences capable of directing the replication and/or the expression of, and operatively linked to a DNA sequence coding for, all or part of mutant creatinase. Suitable host cells include, for example, *E. coli* HB101 (ATCC 33694) available from Pomega (2800 Woods Hollow Road, Madison, Wis., USA), XL1-Blue MRF available from Stratagene (11011 North Torrey Pine Road, La Jolla, Calf. USA) and the like.

Expression vectors may be introduced into host cells by various methods known in the art. For example, transformation of host cells with expression vectors can be carried out by polyethylene glycol mediated protoplast transforrnation method (Sambrook, et al. 1989). However, other methods for introducing expression vectors into host cells, for example, electroporation, biolistic injection, or protoplast fusion, can also be employed.

Once an expression vector containing creatinase variants has been introduced into an appropriate host cell, the host cell may be cultured under conditions permitting expression of the desired creatinase variants. Host cells containing an expression vector which contains a DNA sequence coding for all or part of the mutant creatinase may also be identified by one or more of the following general approaches: DNA hybridization, the presence or absence of marker gene functions, assessment of the level of transcription as measured by the production of creatinase mRNA transcripts in the host cell, and detection of the gene product immunologically, but preferably by identification through enzyme assay (colorimetric detection, etc.).

The present invention also teaches methods for screening of appropriate creatinase variants. The assay conditions chosen to asses enzymatic activity, are adapted to ensure that the expected small enhancements brought about e.g., by a single amino acid substitution, can be measured. This has been accomplished by adjusting the assay conditions such that the wild type (or parent) enzyme activity is close to the lower detection limit. One mode of selection or screening of appropriate mutants with lower Km-values is given in Example 3. Any change or improvement as compared over the wild-type enzyme this way can be clearly detected. Methods to assess long term storage stability as well as short term thermal stress stability are also described in detail in the Examples section.

By creating a replica plate of the clones to be assayed, the clones can be subjected to an array of procedures without loss of viability. For example, many intracellular enzymes require cell lysis before they can be assayed. This procedure could be performed in a screen, and when positives are found, they can be re-grown from the replica plate.

Furthermore, multiple measurements can be made on each sample to account for variability in protein expression levels or to check other key enzyme properties. Additionally, these assays are often done in much the same way the enzyme is traditionally assayed (e.g. spectrophotometrically), making the assay a straightforward technique that can be implemented quickly.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

It is preferred that the polypeptides of the present invention are obtained by production in host cells expressing a DNA sequence coding the mutant creatinase.

However, the polypeptides of the present invention may be obtained by in vitro translation of the mRNA encoded by a DNA sequence coding for the mutant creatinase. For example, the DNA sequences may be synthesized using PCR as described above and inserted into a suitable expression vector, which in turn may be used to in vitro transcription/translation system.

In a preferred embodiment the present invention relates to a method for production of an *Erwinia*-type creatinase variant, the method comprising the steps of cloning a wild-type enzyme, introducing mutations, selecting as compared to the wild-type enzyme variants with improved thermostability or improved creatinase activity, and recombinantly producing said variant The polypeptides produced in these manners may then be isolated and purified to some degree using various protein purification techniques. For example, chromatographic procedures such as ion exchange chromatography, gel filtration chromatography and affinity chromatography may be employed.

The polypeptides of the present invention have been defined by means of determined DNA and deduced amino acid sequencing. Due to the degeneracy nature of the genetic code, which results from there being more than one codon for most of the amino acid residues and stop signals, other DNA sequences which encode the same amino acid sequence as given in SEQ ID NO:2 may be used for the production of the polypeptides of the present invention.

The invention also contemplates a process for producing a creatinase variant of the current invention comprising culturing a host cell of the invention under conditions suitable for production of the mutant creatinase of the invention. For bacterial host cells, typical culture conditions are liquid medium containing the appropriate antibiotic and induction agent. Cultures are shaken or stirred at temperature suitable for optimal production of enzyme, e.g., about 25° C. to about 37° C. Typical appropriate antibiotics include ampicillin, kanamycin, chloroamphenicol, tetracycline and the like. Typical induction agents include IPTG, glucose, lactose and the like.

As discussed, improved variants of creatinase are very important in order to produce appropriate reagents for creatinine and/or creatine assays, e.g. as used in the clinical diagnostic routine. Especially a liquid reagent comprising an improved creatinase meeting improved stability criteria is highly import. In a preferred embodiment the present invention relates to a reagent for determination of creatine (or for the determination of creatinine or for the simultaneous determination of both analytes) comprising an *Erwinia*-type creatinase variant according to the present invention.

In clinical routine nowadays in the determination of an analyte as few reagents as possible, requiring as little handling as possible have to be provided to facilitate measurement for the customer and to reduce the chances for erroneous handling. In a further preferred embodiment the present invention therefore relates to a reagent comprising a creatinase variant according to the present invention and also comprising a sarcosine oxidase and reagents for the detection of hydrogen peroxide.

One of the major applications of the improved creatinase variants in this invention is for the measurement of creatinine and/or creatine in clinical samples. Due to their enhanced overall stability and relatively small Km values for creatine, assays system using these improved creatinase variants e.g., as liquid reagents, are more economic and more robust. In a further preferred embodiment the present invention relates to a method for detection of creatine, the method comprising the steps of a) incubating a sample to be analyzed with b) a reagent comprising a variant of an *Erwinia*-type creatinase, a sarcosine oxidase and reagents for detection of hydrogen peroxide and c) correlating the hydrogen peroxide generated to the concentration of creatinine in said sample.

The reagents for the determination of creatine according to the present invention contains each ingredient in appropriate amounts. Preferred ranges are: creatinase 0.01–100 U/ml, sarcosine oxidase 1–50 U/ml, peroxidase 0.01–30 U/ml, a coupler reagent at 0.1–10 mM, and a color generating substance at 0.1–50 mM.

More preferred ranges are: creatinase 1–50 U/ml, sarcosine oxidase 1–50 U/ml, peroxidase 0.1–10 U/ml, a coupler reagent at 0.1–10 mM, and a color generating substance at 1–30 mM. The buffer system used preferably is a potassium phosphate buffer of 0.1 M with a pH of 7.5 to 8.0 or a 0.05 M TAP-buffer of pH 8.0 to 8.5 (TAP=3-[(tris(hydroxymetbyl)methyl]aminopropane sulfonic acid).

The creatinase from *Erwinia* and variants thereof exhibit an additional important property, i.e. a much lower conductivity. These creatinases can also be used in biosensors similar to those described by Kim et al. (Kim, E. J., et al., Anal. Chim. Acta 394 (1999) 225–231) and by Khan et al. (Khan, G. F. Wernet, W., Anal. Chim.

Acta 351 (1997) 151–158) for online monitoring creatinine/creatine concentration in a sample or a reactor.

The improved creatinase variants of the present invention are described by making reference to substitutions of amino acids from SEQ ID NO:2, the creatinase isolated from *Erwinia* sp. (DSM 97-934).

Sequence comparisons to other known creatinases revealed that the corresponding enzymes isolated from *Actinobacillus* or *Alcaligenes* strains are more than 90 % identical to SEQ ID NO:2. Even more surprisingly, we found that the 7-mer peptide sequence motifs of SEQ ID NO:4, SEQ ID NO:5, SEQ ID NO:6, SEQ ID NO:7, and SEQ ID NO:8 are identical in these creatinases. The same type of substitution(s) as described in the present invention is(are) used to improve these enzymes.

In a preferred embodiment the present invention relates to a variant of *Erwinia* creatinase, which compared to the corresponding wild-type enzyme as isolated from DSM (97-934), is characterized in that said variant comprises at least one amino acid substitution at a position corresponding to a position selected from the group of positions consisting of F59, N130, M203, I278, I304, and F395 of the amino acid sequence shown in SEQ ID NO:2.

In a further preferred embodiment the present invention relates to a variant of an *Alcaligenes* creatinase which compared to the corresponding wild-type enzyme is characterized in that said variant comprises at least one amino acid substitution at a position corresponding to a position selected from the group of positions consisting of N130, M203, I278, I304, and F395 of the amino acid sequence shown in SEQ ID NO:2.

In a further preferred embodiment the present invention relates to a variant of an *Actinobacillus* creatinase which compared to the corresponding wild-type enzyme is characterized in that said variant comprises at least one amino acid substitution at a position corresponding to a position selected from the group of positions consisting of N130, M203, I278, I304, and F395 of the amino acid sequence shown in SEQ ID NO:2.

Preferably, the above described variants of an *Erwinia* creatinase, an Alcaligenes creatinase or of an *Actinobacillus* creatinase in comparison to the corresponding wild-type sequence, comprise 20 amino acid substitutions or less, more preferred 15 amino acid substitutions or less, even more preferred 10 amino acid substitutions or less, and most preferred 6 amino acid substitutions or less.

In the following examples, all reagents, restriction enzymes, and other materials were obtained from Roche Diagnostics, unless specified from other commercial sources, and used according to the indication by suppliers. Operations employed for the purification, characterization and cloning of DNA are well known in the art and can be adapted from published literatures.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Cloning and Expression of *Erwinia* DSM97-934 Creatinase Gene in *E.coli*

The creatinase gene was amplified from *Erwinia* DSM97-934 genome with PCR. Both the amplified DNA fragment and the pKK177-3HB plasmid were digested with the restriction enzymes Eco RI and Hin dIII. The digested products were gel purified and ligated. An aliquot of the ligation reaction mixture was used to transform competent *E. coli* cells, for example *E. coli* HB101 cells. The transformants were subsequently selected on LB plates containing ampicillin. To assay, individual colonies were chosen, grown over night in LB medium (cf. Sambrook et al., 1989, supra) containing ampicillin and subjected to screening.

EXAMPLE 2

Mutating the Wild-type Creatinase from *Erwinia* sp.

In order to improve the enzymes properties the following mutagenesis methods were used to generate creatinase variants: mutagenic PCR, saturation mutagenesis and site directed mutagenesis.

Mutagenic PCR is a method to introduce random point mutations into the elected DNA. This method was performed according to the protocol described by Cadwell and Joyce. (Cadwell, R. C. Joyce, G. F., PCR Methods Appl 3 (1994) 136–40) with some modifications.

The mutagenic PCR was set up as following:

| | |
|---|---|
| Template DNA | 61 fmol (= 40 ng pCT-WT |
| Forward Primer | 40 pmol |
| Reverse Primer | 40 pmol |
| 10 × Taq Puffer | 10 µl (without Mg2+; Roche # 1 699 105) |
| $MgCl_2$ | 7 mM |
| $MnCl_2$ | 0–0.8 mM |
| dATP, dGTP | 0,2 mM (Roche # 1 969 064) |
| dCTP, dTTP | 1 mM (Roche # 1 969 064) |
| Taq DNA polymerase | 5 U(Roche # 1 418 432) |
| $H_2O$ | added to total volume of 100 µl |

The PCR cycling was done with the following conditions:

| | | |
|---|---|---|
| 95° C. | 5 min | |
| 95° C. | 1 min | |
| 46/70° C. | 1 min | 30 |
| 72° C. | 2 min | cycles |
| 4° C. | time span variable, set as appropriate | |

Two generations of mutagenic PCR were performed. First generation was carried out with plasmid pCT-WT, primer ECF21 (5' CAG GAA ACA GAA TTC ATG ACT 3')/HIR21 (5' CCA AAA CAG CCA AGC TTT CAG 3') and an annealing temperature of 46° C. Second round of mutagenic PCR was carried out with plasmid pCTlm24, primer CtextF (5' CAT CGG CTC GTA TAA TGT GTG G 3')/CtextR (5' GCC AAA ACA GCC AAG CTT TCA G 3') and an annealing temperature of 70° C. Each round of mutagenic PCR was performed with several $MnCl_2$ concentrations to obtain different mutagenic rates and therefore different rates of inactive clones.

Mutagenic PCR products were purified using ion exchange techniques (Roche High Pure™ PCR Product Purification Kit #28104) and were eluted in $H_2O$. The purified PCR products and plasmid pKK177-3HB were digested with restriction enzymes Eco RI and HindIII, purified by preparative gel electrophoresis (1% agarose/TAE) and gel extraction with QIAquick Gel Extraction Kit (Quiagen Cat.#28706). Eco RI/HindIII-digested PCR products were ligated into Eco RI/Hind III-digested plasmid vector pKK177-3HB using T4 DNA ligase (Roche #481 220) according to the manual. Ligation reactions were introduced into E. coli HB101 according to the manual for high-efficiency transformation by electroporation (Current protocols in molecular biology, chapter 1.8.4) or into Epicurian Coli®XL1-Blue super competent cells (Stratagene #200236) according to the suppliers manual. Transformants were plated on LB-Agar with 100 µg/ml ampicillin and grown at 37° C., 14 h. The pool with about 50 % active clones were chosen for screening. In each evolution generation, about 3 000 clones were screened.

Saturation Mutagenesis is a method to randomly introduce any of the 20 canonic amino acids into a defined position of the protein using a PCR like method with defined primers containing a random three base stretch. The whole plasmid is amplified using two complementary primers. The parental plasmid (without the mutation) is removed by enzymatic cleavage using Dpn I. For mutagenesis of creatinase genes, QuikChange™ Site-Directed Mutagenesis Kit (Stratagene #200518) was used according to the suppliers manual. Plasmids with mutagenized creatinase genes were introduced into E. coli HB 101 or E. coli XL1-Blue as described above. About 200 clones were screened in each saturation mutagen experiment to ensure sufficient statistical diversity.

To combine several useful mutations in one creatinase mutant the method of site directed mutagenesis was also used. The principle and protocol is similar to saturation mutagenesis, except that defined primers containing the mutated triplet were used.

EXAMPLE 3

Screening and Assay of Erwinia-creatinase and Variants Thereof

The activity assay for creatinase and its variants was performed by using creatine as substrate and a coupled enzymatic reaction according to Guder, W. G., et al., J Clin Chem Clin Biochem 24 (1986) 889–902.

The reaction mixture was set up by combining the following reagents:

| | |
|---|---|
| 90 mM creatine in 0.1 M potassium phosphate buffer, pH 7.8 | 2.5 ml |
| 30 mM 4-Amino-2,3-dimethyl-1-phenyl-3-pyrozoline-5-one | 0.05 ml |
| 143,5 mM 2,4,6-tribrom-3-hydroxybenzoic acid | 0.1 ml |
| sarcosine oxidase (150 U/ml) | 0.1 ml |
| peroxidase (500 U/ml) | 0.02 ml |
| creatinase solution (crude extract) | 0.01 ml |

The assay for creatinase was carried out at 25° C. and at the wavelength of 546 nm for 10 min. ΔE was calculated from the measurement points of 6 to 10 min.

Screening clones of creatinase and its variants was carried out according to the above assay procedure.

Each screening step was performed in 96-well microtiterplates.

Colonies were picked into these plates and grown for 24 h in 200 µl of LB-medium (cf. Sambrook et al., 1989, supra). After cell lysis by addition of 51 µl detergent (B-PER™ Bacterial Protein Extraction Reagent; PIERCE #78248) per well, 10 µl aliquots of the crude extracts were assayed.

In order to screen creatinase variants with lower Km values, creatinase activity of the crude enzyme extract thus obtained was determined. Using an activity determination reagent having only the $15^{th}$ part of the above creatine substrate concentration, the creatinase activity of the same samples was again determined. Any clone wherein the ratio of the two kinds of the activity measures (activity with $\frac{1}{15}$ substrate concentration /activity obtained by conventional method) increased beyond that of a wild type creatinase was selected as a candidate mutant having a lower Km value. For example, the activity screening was done using an optimal creatine concentration (90 mM) and a reduced creatine concentration (6 mM). Comparison of the activity ratios of the two with that obtained using a wild type creatinase leads to the identification of the potentially positive creatinase variants having smaller Km values.

In order to screen for thermostable creatinase variants, the crude extract of each creatinase variant was used to determine initial and residual creatinase activity before and after heat treatment (e.g. 56° C., 30 min). Comparison of the activity ratios of the two experiments of the activity ratio obtained using a wild type creatinase leads potentially positive creatinase variants with enhanced thermostability.

EXAMPLE 4

Mutants of *Erwinia* Creatinase with Improved Properties

The above mentioned screening efforts led to several creatinase variants with enhanced thermostabilities, improved solubilities, lower Km values and/or lower conductivities. These variants are shown in Table 1. The sequences of the primers used in each generation are shown in Table 2.

TABLE 1

Examples of creatinase mutants generated

| Mutant | DNA and amino acid sequence, respectively | Primers used |
|---|---|---|
| CT1m24 | SEQ ID NO: 9 and SEQ ID NO: 10 | ECF21 and HIR 21 |
| CT2m9 | SEQ ID NO: 11 and SEQ ID NO: 12 | CTextF and CTextR |
| CT2m10 | SEQ ID NO: 13 and SEQ ID NO: 14 | CTextF and CTextR |
| CT2m28 | SEQ ID NO: 15 and SEQ ID NO: 16 | CTextF and CTextR |
| CTsd2 | SEQ ID NO: 19 and SEQ ID NO: 20 | CTf3951F and CTf3951R |
| CTqc2 | SEQ ID NO: 17 and SEQ ID NO: 18 | CT59F and CT59R |
| CTsd7 | SEQ ID NO: 21 and SEQ ID NO: 22 | CTf59wF and CTf59wR |

TABLE 2

The sequences of the used primers

| | |
|---|---|
| ECF21 | CAG GAA ACA GAA TTC ATG ACT (SEQ ID NO: 23) |
| HIR21 | CCA AAA CAG CCA AGC TTT CAG (SEQ ID NO: 24) |
| CTextF | CAT CGG CTC GTA TAA TGT GTG G (SEQ ID NO: 25) |
| CTextR | GCC AAA ACA GCC AAG CTT TCA G (SEQ ID NO: 26) |
| CTf3951F | CAT TAC CGG ATT CCC CCT GGG GCC TGA GCA CAA C (SEQ ID NO: 27) |
| CTf3951R | GTT GTG CTC AGG CCC CAG GGG GAA TCC GGT AAT G (SEQ ID NO: 28) |
| CT59F | GCA TCA ATT ACT ACT CTG GAN NNC TGT ACT GCT ATT TCG GCC GC (SEQ ID NO: 29) |
| CT59R | GCG GCC GAA ATA GCA GTA CAG NNN TCC AGA GTA GTA ATT GAT GC (SEQ ID NO: 30) |
| CTf59wF | GCA TCA ATT ACT ACT CTG GAT GGC TGT ACT GCT ATT TCG GCC GC (SEQ ID NO: 31) |
| CTf59wR | GCG GCC GAA ATA GCA GTA CAG CCA TCC AGA GTA GTA ATT GAT GC (SEQ ID NO: 32) |

EXAMPLE 5

Genetic Characterization of *Erwinia* creatinase Mutants with Improved Properties The creatinase mutants with improved properties were genetically characterized, and their DNA and corresponding amino acid sequences are given in SEQ ID NO: 9–22. Table 3 summaries the mutations as identified for each of these creatinase mutant.

TABLE 3

Amino acid substitutions of the creatinase variants with improved properties

| Mutant | Mutations |
|---|---|
| CT1m24 | N130D, I278T |
| CT2m9 | N130D, M203V, I278T |
| CT2m10 | N130D, I278T, F395L |
| CT2m28 | N130D, I304L, I278T |
| CTqc2 | F59W, N130D, I278T |
| CTsd2 | N130D, M203V, I278T, F395L |
| CTsd7 | F59W, N130D, M203V, I278T, F395L |

EXAMPLE 6

Purification of an *Erwinia*-type Creatinase

The method for obtaining the purified creatinase and creatinase variants as selected above from the cell cultures may be any known method, such as the following. After the cells obtained by culturing in a nutrient medium were recovered, the cell pellets were homogenized in 20 mM Tris-HCl (pH 8) using high pressure cell disruption at a pressure of 900 bar to give a crude cell extract. The resulting enzyme extract was then subjected to ion exchange chromatography on DEAE-Sepharose fast flow using a 0.1–0.35 M NaCl gradient for elution. After this separation step, the resulting creatinase fraction may be further separated and purified by e.g. phenylsepharose column chromatography (pharmacia Biotech) to give a standard purified enzyme product. Usually, the end product thus obtained is at least 90 % pure and shows one predominant band in SDS-PAGE corresponding to creatinase. In case SDS PAGE should occasionally reveal a lower degree of purity the purification steps are repeated.

EXAMPLE 7

Characterization of *Erwinia*-creatinase and of Variants Thereof

The characterizations of *Erwinia*-creatinase and its variants included $K_M$ and short therml thermal stress determination as well as determination of the residual activity after incubation at 35° C. for 21 days in CreaPlus buffer.

a) Km determination

For $K_M$ determination, creatinase activity was determined according to the assay procedure described in Example 3 using six different concentrations of creatine substrate: 90 mM, 45 mM, 22.5 mM, 11.3 mM, 5.6 miM and 2.8 mM.

b) Assessment of short term thermal stress stability

The thermoinactivation of the cloned wild type *Erwinia* creatinase and its thermostable mutants was done with purified enzyme or enzyme mutants. The enyme was stressed in concentrated form at an enzyme concentration of 30 U/ml in 0.1 M potassium phosphate buffer (pH 7.8). The (residual) creatinase activity was determined from appropriate dilutions made from this stock solution, as described by Guder et al. supra. The creatinase assay was set up as follows:

| | |
|---|---|
| 0.1 M creatine in 0.1 M potassium phosphate buffer, pH 7.8 | 2.5 ml |
| 30 mM 4-Amino-2,3-dimethyl-1-phenyl-3-pyrozoline-5-one | 0.05 ml |
| 143,5 mM 2,4,6-tribromo-3-hydroxybenzoic acid | 0.1 ml |

-continued

| | |
|---|---|
| sarcosine oxidase (150 U/ml) | 0.1 ml |
| peroxidase (500 U/ml) | 0.02 ml |
| creatinase (dilutions ranging from 0.01 to 5.0 U/ml) | 0.01 ml |

The assay was carried out at 25° C. and at the wavelength of 546 nm for 10 min. ΔE was calculated from the measurement points of 6 to 10 min.

After the initial enzyme activities were determined, all samples were subjected to thermoinactivation by incubating in 0.1 M potassium phosphate buffer at 56° C. for 20 minutes. The residual activity of each heat-treated sample was determined as described above. An thermo-index (initial activity/residual activity) for each tested sample was used for the enzyme thermostability evaluation. As shown in Table 4 (or FIG. 4), all mutants CT1m24, CT2m10, CT2m28, CTsd2, CTqc2, CTMm9 and CTsd7 are more thermostable than the wild type *Erwinia* creatinase.

Table 4 summarizes the characterization results $K_M$ and $T_M$ values of the novel creatinase mutants compared to native creatinase from *Erwinia* sp.

TABLE 4

Characteristics of creatinase and creatinase mutants

| Mutant | $K_M$ | Thermo-Index |
|---|---|---|
| Wildtyp | 4.3 mM | 0.7% |
| CT1m24 | 8.2 mM | 6.3% |
| CT2m10 | 3.4 mM | 3.9% |
| CT2m28 | 4.0 mM | 3.9% |
| CTsd2 | 2.1 mM | 39.7% |
| CTqc2 | 6.6 mM | 50.8% |
| CT2m9 | 6.3 mM | 62.9% |
| CTsd7 | 2.0 mM | 69.2% |

As shown in the above table, the novel creatinase mutants CTsd2 and CTsd7 of the present invention have much lower Km values and much enhanced thermostability as compared to the wild type *Erwinia* creatinase.

EXAMPLE 8

Application of an Improved Creatinase Variant of a Determination for Creatinine/creatine Concentration The improved creatinase variant of the present invention is according to standard procedures used in the determination of a creatine concentration upon combining it with a sacrosine oxidase, a peroxidase and other compositions for detection of hydrogen peroxide.

Moreover, if a creatinase is also used, the concentration of creatinine can also be determined using the improved creatinase variants according to the present invention. In case in the sample investigated creatine as well as creatinine are present, the sum of both analytes is measured.

The reagent for the determination of creatine according to the present invention contains each the ingredients in an optimized concentration. An example is a reagent comprising creatinase at 16 U/ml, sacrosine oxidase at 9.8 U/ml, peroxidase at 0.81 U/ml, a coupler reagent at 0.65 mM, and a color generating substance at 7.0 mM. The buffer system used here is a potassium phosphate buffer with a concentration at 0.1 M and pH7.8. The assay usually is carried out at 25° C. and color development is measured at the wavelength of 546 nm for 10 minutes. ΔE is calculated from the measurement points in the linear region and used for determining creatine concentration.

What is claimed is:

1. A variant creatinase having creatinase activity comprising at least one amino acid substitution at a position corresponding to an amino acid position of SEQ ID NO: 2 selected from the group of positions consisting of N130, M203, I278, I304, and F395, wherein the variant creatinase comprises a sequence with 20 or less adding acid substitutions compared to SEQ ID NO:2.

2. The creatinase according to claim 1 wherein at least one substitution is at an amino acid position corresponding to position N130 or I278.

3. The creatinase according to claim 2, wherein the creatinase is more stable than wild type *Erwinia* creatinase of SEQ ID NO:2 at 56° C.

4. The creatinase according to claim 1 wherein at least one amino acid substitution is at an amino acid position corresponding to positions I304 or F395.

5. The creatinase according to claim 4, wherein the creatinase exhibits a lower Km-value in the enzymatic cleavage of creatine than wild-type *Erwinia* creatinase of SEO ID NO:2.

6. A variant creatinase having creatinase activity comprising at least two amino acid substitutions at positions corresponding to amino acid positions of SEQ ID NO: 2, the positions being selected from the group of positions consisting of N130, M203, I278, I304, and F395, wherein at least one amino acid substitution is at position N130 or I278 and at least one substitution is at position I304 or F395, wherein the variant creatinase comprises a sequence with 20 or less amino acid substitutions compared to SEQ ID NO:2.

7. The creatinase according to claim 6 wherein the creatinase is more stable than wild type *Erwinia* creatinase of SEQ ID NO:2 at 56° C. and the creatinase exhibits a lower Km-value in the enzymatic cleavage of creatine than wild type *Erwinia* creatinase of SEQ ID NO:2.

8. A composition comprising the modified creatinase of claim 1, sarcosine oxidase and reagents for the detection of hydrogen peroxide.

9. A composition comprising the modified creatinase of claim 6, sarcosine oxidase and reagents for the detection of hydrogen peroxide.

* * * * *

UNITED STATES PATENT AND TRADEMARK OFFICE
CERTIFICATE OF CORRECTION

PATENT NO. : 6,958,231 B2
DATED : October 25, 2005
INVENTOR(S) : Shao Zhixin et al.

It is certified that error appears in the above-identified patent and that said Letters Patent is hereby corrected as shown below:

Column 18,
Line 18, delete "adding" and insert -- amino --.
Line 33, delete "SEO" and insert -- SEQ --.

Signed and Sealed this

Thirty-first Day of January, 2006

JON W. DUDAS
*Director of the United States Patent and Trademark Office*